(12) United States Patent
Allendorf et al.

(10) Patent No.: US 9,347,923 B1
(45) Date of Patent: May 24, 2016

(54) COLOROMETRIC DETECTION OF WATER USING MOF-POLYMER FILMS AND COMPOSITES

(71) Applicant: Sandia Corporation, Albuquerque, NM (US)

(72) Inventors: Mark D. Allendorf, Pleasanton, CA (US); Albert Alec Talin, Dublin, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/595,034

(22) Filed: Jan. 12, 2015

(51) Int. Cl.
*G01N 31/22* (2006.01)
*G01N 31/00* (2006.01)

(52) U.S. Cl.
CPC .................................. *G01N 31/222* (2013.01)

(58) Field of Classification Search
CPC ..... G01N 31/222; G01N 31/00; G01N 31/22; G01N 21/81; G01N 21/78; G01N 21/77; G01N 21/75; G01N 21/00; F21K 5/02; F21K 5/023; F21K 5/00
USPC ...................................................... 436/41, 39
See application file for complete search history.

(56) References Cited

U.S. PATENT DOCUMENTS

| | | | | |
|---|---|---|---|---|
| 2009/0209420 | A1* | 8/2009 | Kalgutkar | B32B 5/16 503/201 |
| 2012/0040471 | A1* | 2/2012 | Chen | C07C 7/12 436/172 |
| 2012/0178173 | A1* | 7/2012 | Li | C07F 3/003 436/106 |

OTHER PUBLICATIONS

Kreno Lauren E., et al, Metal-Organic Framework Materials as Chemical Sensors, Chem. Rev., 2012, vol. 112, pp. 1105-1125.*

Li, Jian-Rong, Metal-Organic Framework for Separations, Chemical Reviews, ACS Publication, 2012, 112, 869-932.*

Allendorf, Mark et al, Deposition of Thin Films for Sensor Applications, Metal-Organic Frameworks: Application from Catalysis to Gas Storage, Wiley-VCH Verlag GmbH & Co. KGaA, 2011, pp. 310-335.*

Chen, Z., et al., "Humidity sensors: A review of materials and mechanisms", Sensor Letters, vol. 3, (2005), pp. 274-295.

Chui, S., et al., "A chemically functionalizable nanoporous material [Cu3(TMA)2(H2O)3]n", Science, vol. 283, (1999), pp. 1148-1150.

Kreno, L. E., et al., "Metal-organic framework thin film for enhanced localized surface plasmon resonance gas sensing", Analytical Chemistry, vol. 82, No. 19, (2010), pp. 8042-8046.

Kusgens, P., et al., "Characterization of metal-organic frameworks by water adsorption", Microporous and Mesoporous Materials, 120, (2009), pp. 325-330.

Robinson, A. L., et al., "Ultrasensitive humidity detection using metal-organic framework-coated microsensors", Anal. Chem., 84, (2012), pp. 7043-7051.

Wang, Q. M., et al., "Metallo-organic molecular sieve for gas separation and purification", Microporous and Mesoporous Materials, 55, (2002), pp. 217-230.

* cited by examiner

*Primary Examiner* — Christine T Mui

(74) *Attorney, Agent, or Firm* — Blakely, Sokoloff, Taylor & Zafman, LLP

(57) ABSTRACT

A method including exposing a mixture of a porous metal organic framework (MOF) and a polymer to a predetermined molecular species, wherein the MOF has an open metal site for the predetermined molecular species and the polymer has a porosity for the predetermined molecular species; and detecting a color change of the MOF in the presence of the predetermined molecular species. A method including combining a porous metal organic framework (MOF) and a polymer, wherein the MOF has an open metal site for a predetermined molecular species and the polymer has a porosity for the predetermined molecular species. An article of manufacture including a mixture of a porous metal organic framework (MOF) and a polymer, wherein the MOF has an open metal site for a predetermined molecular species and the polymer has a porosity for the predetermined molecular species.

13 Claims, 1 Drawing Sheet

COLOROMETRIC DETECTION OF WATER USING MOF-POLYMER FILMS AND COMPOSITES

STATEMENT OF GOVERNMENT RIGHTS

This invention was developed under Contract DE-AC04-94AL85000 between Sandia Corporation and the U.S. Department of Energy. The U.S. Government has certain rights in this invention.

FIELD

Metal organic framework and detection devices and techniques.

BACKGROUND

Detection of liquid and gaseous water is important in many industries, including pharmaceuticals, microelectronics fabrication, food processing, and chemical manufacturing. Electronic sensors based on chemiresistors, microcantilevers, and surface acoustic wave (SAW) devices have been demonstrated and are capable of detecting water vapor at sub-ppb levels in real time. Such sensors generally require power to operate and potentially cumbersome data collection and analysis (either in hardware or software) to produce a result. In some applications, these are disadvantages, particularly in cases with limited power accessibility or limited space availability. Another disadvantage is that not all water-sensitive coatings used to enhance sensitivity and/or selectivity are stable in both humid environments and liquid-phase water.

Although electronic sensors can provide real-time information and high sensitivity, often the only information required is a positive or negative indication that water is present. In this case, a simple visual indicator is highly desirable. For example, some versions of Drierite™ (anhydrous calcium sulfate or gypsum) are mixed with a small amount of cobalt(II)chloride, which changes color from blue to pink when exposed to moisture. 3M markets "Water Contact Indicator Tape," which changes from white to red when in contact with liquid water. Disadvantages of these materials are their relatively limited capacity (10-14 wt % for Drierite™) and inability to detect both liquid and vapor-phase water.

SUMMARY

In one embodiment, a method is described exposing a mixture of a porous metal organic framework (MOF) and a polymer to a predetermined molecular species and detecting a color change of the MOF in the presence of the predetermined molecular species. In another embodiment, a method of manufacture is described including combining a porous MOF and a polymer wherein the MOF has an open metal site for a predetermined molecular species and the polymer has a porosity for the predetermined molecular species. In a further embodiment, an article of manufacture is described including a mixture of a porous MOF and a polymer.

BRIEF DESCRIPTION OF THE DRAWINGS

The invention may best be understood by referring to the following description and accompanying drawings that are used to illustrate embodiments of the invention. In the drawings.

DETAILED DESCRIPTION

Figure 1:
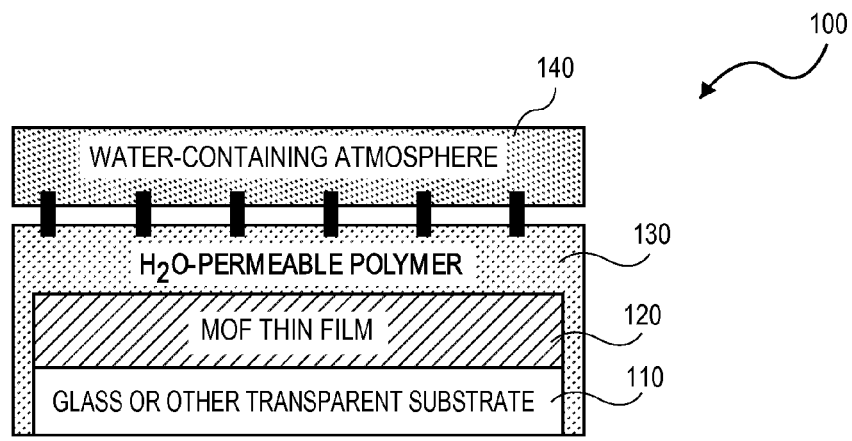
FIG. 1 shows a cross-sectional side view of an embodiment of an article of manufacture operable to detect a presence of water.

In one embodiment, a method is disclosed. The method includes exposing a mixture of a porous metal organic framework (MOF) and a polymer to a predetermined molecular species. A suitable MOF has an open metal site for a predetermined molecular species and the polymer has a porosity for the predetermined molecular species. The method also includes detecting a color change of the MOF in response to a presence of the predetermined molecular species. A representative molecular species includes water such as liquid or gaseous water making the method suitable for detecting the presence of liquid or gaseous water. In another embodiment, a method of manufacture is disclosed. The method includes combing a porous MOF and a polymer when the MOF has an open metal site for a predetermined molecular species and the polymer has a porosity for the predetermined molecular species. In a still further embodiment, an article of manufacture is described. An article of manufacture includes a mixture of a porous MOF and a polymer wherein the MOF has an open metal site for a predetermined molecular species and the polymer has a porosity for the predetermined molecular species. Such mixture may be disposed on a substrate as a single mixture or one of a plurality of mixtures, each mixture comprising a mixture of a MOF and a polymer.

In one embodiment, a MOF is a nanoporous compound including metal ions or clusters coordinated to organic ligands. Suitable metal ions or clusters include copper ions (e.g., $Cu^{2+}$), and ions of chromium (Cr), iron (Fe), nickel (Ni), molybdenum (Mo) and ruthenium (Ru). In one embodiment, a suitable MOF includes $Cu_3(BTC)_2$ also known as HKUST-1. In another embodiment, a suitable MOF is a MOF such as HKUST-1 or other MOF that has an open metal site making the MOF susceptible to a reaction with water or other molecular species such as, but not limited to, ammonia, phosphine or hydrogen sulfide. In one embodiment, a MOF such as HKUST-1 is prepared to have an open metal site by exposing the MOF to an elevated temperature under pressure (e.g., 180° C. under vacuum).

With respect to detecting the presence of liquid or vapor water, MOFs are particularly advantageous for detecting applications because of their permanent porosity, synthetically tailorable structure (both pore geometry and chemical environment), ultrahigh surface areas, and thermal and chemical stability. HKUST-1 is dark blue/purple in the absence of water and turquoise blue when exposed to water. Its reaction with water is extremely rapid; thin films and the surfaces of powders will change color within seconds of exposure to atmospheric water. HKUST-1 has a water capacity as high as 41 weight percent. HKUST-1 will decompose if immersed in liquid water. Thus, in one embodiment, the MOF is mixed with a polymer material and the mixture (combination of MOF and polymer) is operable as a colorometric sensor. A suitable polymer to be combined with a MOF is one that has a porosity for a molecular species such as water, ammonia, phosphine or hydrogen sulfide.

In one embodiment, a MOF and a polymer having a porosity for a predetermined molecular species (e.g., water, ammonia, phosphine) is operable as an article of manufacture to detect a presence of the molecular species. The combination may be a mixture of the MOF and the polymer or respective layers of the MOF and the polymer. FIG. 1 shows a cross-sectional side view of an article operable to detect the presence of water. Article 100 includes substrate 110 that is a solid substrate such as a glass, plastic, metal, tape, paper or wood. In one embodiment, substrate 110 is a glass or other transparent substrate. Disposed on a surface of substrate 110 (a top surface as viewed) is MOF 120 as a thin film. Disposed on MOF 120 is a film of polymer 130 that is a water permeable polymer such as polydimethylsiloxane (PDMS) or polystyrene. FIG. 1 shows a moisture-containing atmosphere 140 infiltrating polymer 130.

Figure 2:
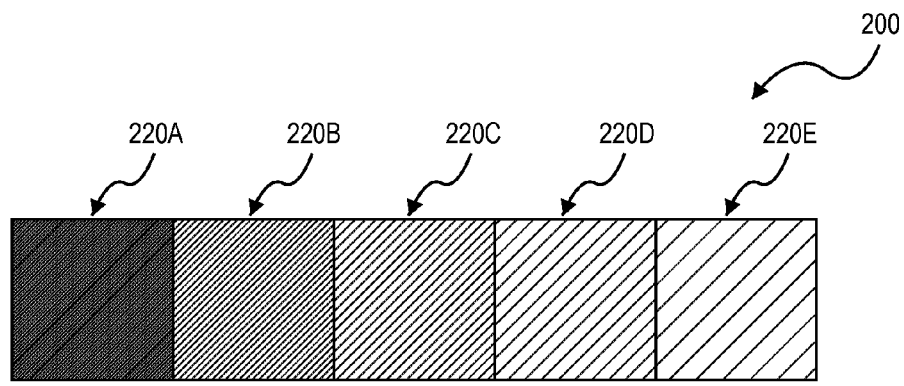
FIG. 2 shows a top view of an embodiment of an article of manufacture including a substrate having a series of MOF films of the same MOF material with polymers of different water permeability disposed on the MOF films.

The article may be used to detect a presence of a molecular species and, in another embodiment, detect a time of exposure of the article to the molecular species. Detecting of a time of exposure may be achieved by a single mixture of a MOF and a polymer wherein a color of the MOF changes to a first color on exposure to molecular species such as water and also changes to at least a second color over continued exposure to the molecular species (i.e., changes color over time). In another embodiment, the article of a mixture of a MOF and a polymer is a first mixture that may be combined with a second mixture of a MOF and a polymer, wherein such second mixture has a MOF with a different affinity for a molecular species than the MOF of the first mixture or the polymer has a different porosity for the molecular species than the first polymer. In one embodiment, the mixture may be disposed on a solid substrate. The mixture may be singly disposed on the substrate or is a first mixture on a substrate comprising at least one other mixture of a MOF and a polymer, wherein such other mixture has a MOF with a different affinity for a molecular species than the MOF of the first mixture or the polymer has a different porosity or permeability for the molecular species than the polymer of the first mixture. FIG. 2 shows a schematic top view of an article including a substrate having a series of MOF films of the same MOF (e.g., HKUST-1) coated with polymers having different permeabilities or porosities for water disposed on the MOF films. FIG. 2 shows article 200 including substrate 210 of, for example, a tape having a side (e.g., top side as viewed) coated with a MOF (e.g., HKUST-1) and areas 220A, 220B, 220C, 220D and 220E coated with polymers having different permeabilities (different from one another) with respect to water. Article 200 may be used to monitor an exposure time to water with for example, area 220A including a polymer with a high permeability for water and area 220E including a polymer with a lower permeability for water and areas 220B-220D having permeabilities that progressively decline from 220B to 220D.

With regard to polymers of different porosities or permeabilities for a molecular species, Table 1 shows the water permeability for a variety of polymers that may be combined (mixed) with a MOF to form an article of manufacture that is a detector or sensor for a presence of water.

TABLE 1

Water vapor permeability and water vapor/$N_2$ selectivity for various polymers at 30° C. extrapolated to water vapor activity 0.

| Polymer | Abbreviation | $H_2O$ Permeability [Barrer] | Selectivity [$H_2O/N_2$] | Reference $H_2O$ | $N_2$ |
|---|---|---|---|---|---|
| Polyethylene | (PE) | 12 | 5.71 | 14 | 12 |
| Polyvinylalcohol | (PVA) | 19 | 33,300 | 14 | 12 |
| Polypropylene | (PP) | 68 | 230 | 14 | 12 |
| Polyamide 6 (Nylon 6) | (PA-6) | 275 | 11,000 | 10 | 12 |
| Polyvinylchloride | (PVC) | 275 | 12,500 | 25 | 12 |
| Polyacrylonitril | (PAN) | 300 | 1,875,000 | 10 | 10 |
| Polyimide (Kapton) | (PI) | 640 | 5,333,300 | 25 | 12 |
| Polystyrene | (PS) | 970 | 400 | 14 | 12 |
| Polycarbonate | (PC) | 1,400 | 4,700 | 10 | 12 |
| Polysulfone | (PSF) | 2,000 | 8,000 | 10 | 26 |
| Natural rubber | (NR) | 2,600 | 300 | 10 | 26 |
| Polyethersulfone | (PES) | 2,620 | 10,480 | 10 | 27 |
| Polyphenyleneoxide | (PPO) | 4,060 | 1,070 | 25 | 12 |
| Cellulose acetate | (CA) | 6,000 | 24,000 | 14 | 12 |
| Sulfonated polyethersulofon | (SPES) | 15,000 | 214,300 | 27 | 27 |
| Ethyl cellulose | (EC) | 20,000 | 6,060 | 25 | 26 |
| Polydimethylsiloxane | (PDMS) | 40,000 | 140 | 10 | 12 |
| Sulfonated polyetheretherketon | (SPEEK) | 61,000 | 10,166,700 | 28 | 28 |
| $1000_{PEO}40_{PBT}60$ | (PEO-PBT) | 104,000 | 40,000 | 29 | |

EXAMPLE 1

MOF-Polymer Composite.

A small amount of the activated (i.e., fully dried) MOF powder was covered with a few drops of the polymer polydimethylsiloxane (PDMS) in an organic solvent; the solvent was allowed to evaporate. PDMS has a relatively high water permeability. The color of this material changes slowly over a period of one hour upon exposure to atmospheric water vapor from a deep purple color at time zero to less deep purple at time 11 minutes to dark blue at time 35 minutes to light blue at time 60 minutes.

EXAMPLE 2

Figure 3:
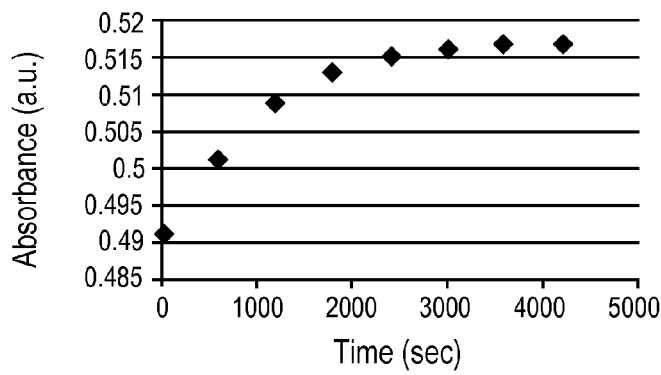
FIG. 3 shows a graph of light absorbance overtime at 450 nm of an HKUST-1 MOF mixed with polystyrene.

A small amount of MOF which the powder was physically mixed with a solution of polystyrene (PS) to create a composite that also displays time-dependent color changes upon exposure to atmospheric water. As seen in FIG. 3, the light absorbance at 450 nm gradually increases as a function of time; similar behavior is seen using the PDMS-MOF material referenced in Example 1. Since polymers with water permeability varying over four orders of magnitude are available (see Table 1) and the thickness of the polymer layer can be varied, HKUST-1/polymer composites that have different time constants for turning color when exposed to water vapor. This would allow the user to estimate the time of exposure. Alternatively, if the time of exposure were known and constant, the concentration of water could be estimated by using a series of MOFs mixed with polymers of different permeability.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated in the figure to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description, various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
    exposing (1) a first mixture of a first porous metal organic framework (MOF) and a first polymer and (2) a second mixture of a second porous MOF and a second polymer to a predetermined molecular species, wherein each of the first MOF and the second MOF has an open metal site for the predetermined molecular species and each of the first polymer and the second polymer has a different permeability for the predetermined molecular species; and
    detecting a color change of the first mixture and the second mixture in the presence of the predetermined molecular species.

2. The method of claim 1, wherein the predetermined molecular species is water.

3. The method of claim 1, wherein detecting a color change depends on a time of exposure to the predetermined species.

4. The method of claim 1, wherein the detecting a color change comprises detecting a first color change of the first mixture after a first period of time and a second color change of the second mixture after a different second period of time.

5. The method of claim 1, wherein one of the first polymer and the second polymer comprises polydimethylsiloxane.

6. The method of claim 5, wherein the other of the first polymer and the second polymer comprises polystyrene.

7. The method of claim 1, wherein the first mixture and the second mixture are applied to a substrate.

8. A method comprising:
    combining a first porous metal organic framework (MOF) and a first polymer to form a first mixture;
    combining a second porous MOF and a second polymer to form a second mixture;
    disposing the first mixture on a first area of a substrate and the second mixture on a different second area of the substrate,
    wherein each of the first MOF and the second MOF has an open metal site for a predetermined molecular species and the first polymer has a permeability for the predetermined molecular species that is different than a permeability of the second polymer for the predetermined molecular species.

9. The method of claim 8, wherein the predetermined molecular species is water.

10. The method of claim 8, wherein one of the first polymer and the second polymer comprises polydimethylsiloxane.

11. The method of claim 8, wherein one of the first polymer and the second polymer comprises polystyrene.

12. An article of manufacture comprising a first mixture of a first porous metal organic framework (MOF) and a first polymer and a second mixture of a second porous MOF and a second polymer, wherein each of the first MOF and the second MOF has an open metal site for a predetermined molecular species and the first polymer has a permeability for the predetermined molecular species that is different than a permeability of the second polymer for the predetermined molecular species.

13. The article of manufacture of claim 12 further comprising a substrate, wherein each of the first mixture and the second mixture is disposed on the substrate.

* * * * *